United States Patent [19]

Beelen et al.

[11] Patent Number: 5,744,671
[45] Date of Patent: Apr. 28, 1998

[54] PROCESS FOR THE PREPARATION OF AN ALKYL BENZENE

[75] Inventors: Henri J. H. Beelen, Heerlen, Netherlands; Geert I. V. Bonte, Diepenbeek, Belgium; Michiel Cramwinckel, 's-Hertogenbosch; Henricus A. M. Duisters, Budel, both of Netherlands; Johan G. D. Haenen, Hasselt, Belgium

[73] Assignee: DSM N.V., Heerlen, Netherlands

[21] Appl. No.: 435,314

[22] Filed: May 5, 1995

[30] Foreign Application Priority Data

Nov. 5, 1992 [NL] Netherlands ............... 9201932

[51] Int. Cl.$^6$ ............... C07C 5/367; C07C 5/42; C07C 5/41
[52] U.S. Cl. ............... 585/430; 585/431; 585/433; 585/434
[58] Field of Search ............... 585/431, 433, 585/434, 430

[56] References Cited

U.S. PATENT DOCUMENTS

| | | | |
|---|---|---|---|
| 2,289,916 | 7/1942 | Komerewsky | 585/431 |
| 3,903,185 | 9/1975 | Vogel et al. | |
| 4,029,715 | 6/1977 | Rieve et al. | 585/431 |
| 4,308,413 | 12/1981 | De Graaf et al. | 585/434 |
| 5,321,180 | 6/1994 | Davis | 585/431 |

FOREIGN PATENT DOCUMENTS 2207103  6/1974  France .

Primary Examiner—Glenn Caldarola
Assistant Examiner—Thuan D. Dang
Attorney, Agent, or Firm—Cushman Darby & Cushman IP Group of Pillsbury Madison & Sutro, LLP

[57] ABSTRACT

The invention relates to a process for the preparation of an alkyl benzene by catalytic dehydrogenation of the corresponding alkenyl cyclohexene in the gas phase in the presence of a diluent. A characteristic feature is that at least a part of the alkyl cyclohexane in the reaction product is used as diluent. Hydrogen can be used as an additional diluent according to the invention.

6 Claims, No Drawings

PROCESS FOR THE PREPARATION OF AN ALKYL BENZENE

The invention relates to a process for the preparation of an alkyl benzene by catalytic dehydrogenation of the corresponding alkenyl cyclohexene in the gas phase in the presence of a diluent.

Such a process is known from EP-B-22,297, which describes how an alkenyl cyclohexene is passed over a dehydrogenation catalyst and the gaseous reaction product is cooled and condensed. For a number of applications it has been found that the presence of byproducts may interfere with further use of the condensed product that is obtained. This can be overcome by purification of the reaction product by means of distillation, yielding a purified alkyl benzene as bottom stream and an alkyl cyclohexane (being the most important byproduct besides the hydrogen) as top stream. To restrict losses, the distillation conditions are to be set so that the top product obtained is (virtually) free of the alkyl benzene main product.

Another drawback of the above-mentioned process is the fact that, when an inert gas is used as diluent (which has a favourable effect on the reaction equilibrium and thus on process economy), the $H_2$ gas released during the reaction is contaminated with this inert dilution gas, so that the $H_2$ gas released is of a low quality.

The invention provides a process which does not have these drawbacks and in which the alkenyl cyclohexene is converted to the corresponding alkyl benzene in an economically attractive manner.

According to the invention this is achieved in that at least a part of the alkyl cyclohexane in the reaction product is used as diluent. This is understood to mean that at least a part of the alkyl cyclohexane in the reaction product is returned to the catalytic dehydrogenation. This yields a number of advantages, which can be described as follows:

a) Since the volume flow passing through the reactor is larger in relation to the alkenyl cyclohexene to be converted, a smaller temperature rise occurs (the dehydrogenation is exothermic), which affects temperature and temperature control as well as reactor design. The reactor design can be changed from a cooled 'tubular reactor' into an adiabatically operated fixed-bed reactor.

b) Since no inert gas is used as diluent, the $H_2$ gas that is released is purer, and thus of a higher quality.

Additional thereto also at least a part of the hydrogen present in the reaction product can be used as diluent. It has been found that the presence of hydrogen has a favourable effect on the service life and the stability of the catalyst, possibly due to the effect on carbon formation.

According to the invention at least a part of the alkyl cyclohexane byproduct present in the reaction product is used as diluent. This byproduct is preferably separated from the reaction product by distillation, as top stream. An added advantage is that the quality requirements to be met by the top stream of such a distillation can be less stringent, particularly because of the recycle to the catalytic dehydrogenation. This also has as a consequence that a part of the alkyl cyclohexane that is returned is reconverted in the catalytic dehydrogenation to the desired alkyl benzene end product, so that this also has a positive effect on the selectivity of the conversion.

The dehydrogenation according to the invention is carried out in the presence of a noble metal catalyst. As such use can be made for instance of platinum, palladium, ruthenium or iridium.

Preferably, use is made of palladium as catalytically active material, it having been found that in contact with palladium the alkenyl cyclohexene is converted to alkyl benzene with a very high selectivity.

Preferably, the noble metal catalyst is used on a non-acidic carrier. When an acidic carrier material is used, for instance alumina, the catalyst does have a very high initial activity, but this activity decreases very rapidly. As non-acidic carrier material use can be made in the first place of basic substances such as oxides, hydroxides or carbonates of calcium and/or magnesium, or barium sulphate, but use can also be made of neutral carrier materials, such as carbon or neutral silicon oxide. Preferably, magnesium oxide is used as carrier material. Calcium oxide, too, is suitable as carrier material.

In the process according to the invention the amount of catalyst per amount of alkenyl cyclohexene to be converted can be varied within broad limits, for instance such amounts that the space velocity, expressed as liter of liquid alkenyl cyclohexene per liter of catalyst per hour (LHSV), is 0.01 to 500. Preferably, space velocities between 0.5 and 50 are chosen. Likewise, the amount of catalytically active noble metal in the catalyst can be varied within broad limits, for instance from 0.01–10 wt. % noble metal, calculated on the total weight of the catalyst. The amount of noble metal in the catalyst preferably amounts to 0.4–4 wt. %, calculated relative to the total weight of the catalyst. Catalyst compositions of 0.5–3 wt. % palladium on magnesium oxide as carrier material have been found to be particularly suitable.

Applicant has found that when the activity decreases the catalyst can in a simple manner be regenerated, and its original activity restored, by passing over air or other oxygen-containing gases.

The process according to the invention is preferably carried out at atmospheric pressure. The use of elevated pressure is possible, but does not give any added advantages. Moreover, the dehydrogenation equilibrium is adversely affected by the use of higher pressures.

The process temperature lies in general between 200°–375° C. Higher temperatures are possible, but catalyst deactivation and decomposition reactions start to predominate. At lower temperatures the formation of the byproduct alkylcyclohexane become more predominante. The temperature preferably lies between 250°–350° C.

As starting materials in the process according to the invention use may be made of various alkenyl cyclohexenes, for instance vinyl cyclohexene, isopropenyl cyclohexene and alkyl-substituted derivatives thereof. These substances can be obtained in a known manner by dimerization and codimerization of conjugated diolefins. Thus, for instance, vinyl cyclohexene can be obtained by dimerization of butadiene, isopropenyl cyclohexene by codimerization of butadiene and isoprene, and methyl isopropenyl cyclohexene by dimerization of isoprene. The invention preferably relates to a process for the preparation of ethyl benzene starting from vinyl cyclohexene.

Applicant has found that the presence of peroxides, in particular hydroperoxides, in the alkenyl cyclohexene to be converted has a negative effect on the service life of the catalyst. Preferably, therefore, use is made of an alkenyl cyclohexene containing less than 5 ppm peroxides. Such an alkenyl cyclohexene which contains practically no peroxides can be prepared by purifying technical-grade alkenyl cyclohexene to remove the peroxides and keeping it under conditions in which oxygen is excluded virtually completely. Peroxides can be removed from alkenyl cyclohexene in a known manner, for instance by selective hydrogenation, thermal decomposition, or distillation over a reducing substance, such as triphenyl phosphine. Purification of the alkenyl cyclohexene, by passing it over a carbon column, can also be applied.

In the process according to the invention the alkenyl cyclohexene feed is (virtually) completely converted into a product consisting predominantly of alkyl benzene. This product can be separated off from the reaction mixture, which contains diluent besides reaction product, in a known manner, for instance by purification by means of distillation. In many cases the isolated main product can be used directly, without further processing, for further conversions. The dehydrogenation product of vinyl cyclohexene, for instance, which consists practically entirely of ethyl benzene, can be converted directly to styrene. The dehydrogenation product of isopropenyl cyclohexene, i.e. isopropyl benzene, can be used as starting material for the preparation of α-methyl styrene, or be converted to phenol by oxidation. In the same way methyl isopropyl benzene, obtained from methyl isopropenyl cyclohexene, can be used for the preparation of methyl phenol, among other things.

The amount of diluent to be used depends on the type of diluent used. The alkenyl cyclohexene/alkyl cyclohexane ratio is normally 10:1 to 1:10, preferably 5:1 to 1:5. If additional hydrogen is used, in general a molar ratio of alkenyl cyclohexene/hydrogen of 2:1 to 1:100, preferably a ratio of 2:1 to 1:10, is used.

During the start-up of the catalytic dehydrogenation it may be advantageous that the diluent also contains an inert gas. As the process proceeds, the inert gas may be replaced by the diluent according to the invention, allowing to take full advantage of the invention.

Preferably, in the diluent also the alkyl benzene formed is present. As a result, the above-mentioned alkenyl cyclohexene/diluent gas ratio can simply be set. Another result is that the adiabatic temperature rise due to the reaction can simply be kept low (preferably 5°–25° C.), so that a simple reactor design can be used: where the state of the art required a tubular reactor (a reactor comprising a plurality of thin tubes (catalyst filled) and external cooling), now the reactor can be an adiabatic bed reactor. This makes for a vastly simplified reactor design, which greatly offsets the additional costs of the recycle of such a diluent. Moreover, upgrading of the reaction product may be simpler, for the top stream leaving the section where purification by distillation takes place, no longer has to meet high purity requirements. Indeed, the top stream still contains, according to the embodiment as sketched, a substantial portion of the alkyl benzene present in the distillation feed. Since this procedure can be applied also during starting up, the use of an inert gas has become absolutely superfluous in this preferred embodiment.

The invention will be elucidated in the following comparative experiment and in the examples.

COMPARATIVE EXPERIMENT A

A fixed-bed reactor with a diameter of 5.2 cm, cooled by means of an oil bath and charged with 250 ml of 2.5% Pd/MgO catalyst, was fed with 250 ml/hr of 4-vinyl cyclohexene (VCH) at a reactor temperature of 240° C. The VCH was diluted with nitrogen (molar ratio 3:1). Under these conditions all vinyl cyclohexene was converted. The selectivity to ethyl benzene was 96 mol%. The $H_2$ formed in dehydrogenation could not simply be isolated in pure form by means of a gas/liquid separation due to the nitrogen inert dilution. After cooling, the liquid reactor product contained 4 mol% ethyl cyclohexane. The reaction product obtained was fed to a packed distillation column having a diameter of 7 cm and a length of 1 m.

To ensure that not more than 100 ppm of ethyl cyclohexane was present in the ethyl benzene during purification by distillation and that not more than 1% of the ethyl benzene was lost with the top stream, 50 separation stages were necessary as well as a reflux ratio of 30 at a top pressure of 10 KPa.

When the reactor cooling was not used, an adiabatic temperature rise of about 120° C. took place, which very rapidly resulted in catalyst deactivation as well as carbonization on the catalyst.

EXAMPLE I

The set-up of comparative experiment A was fed with 250 ml/hr of 4-vinyl cyclohexene. The reactor cooling had been switched off and the reactor was operated adiabatically. The inlet temperature was 240° C. Since (a portion of) the top stream leaving the distillation column, containing about 12.5 wt. % ethyl cyclohexane and 87.5 wt. % ethyl benzene, was recycled to the reactor, the temperature rise could be restricted. Depending on the recycle ratio, the adiabatic temperature rise was 60° C. (at R=1.5), 40° C. (at R=3) and 15° C. (at R=10), R being defined as the amount of recycle per amount of VCH fed to the dehydrogenation reactor. In all cases conversion was complete; the selectivity was 96 mol%. As no $N_2$ was present, pure $H_2$ could be recovered by means of a simple gas/liquid separation. Purification by distillation could be simplified considerably. At an R of 1.5 and atmospheric pressure only 20 trays and a reflux ratio of 4 were found to be needed to achieve the same ethyl benzene purity as in comparative experiment A. The top stream from the distillation column, containing ethyl cyclohexane and ethyl benzene, was returned to the dehydrogenation reaction. It was found that the ethyl cyclohexane present in the reactor was in part dehydrogenated to ethyl benzene. This has been studied in greater detail, the results being described in example II.

EXAMPLE II

In a separate experiment, using the set up of comparative experiment A, the effect was examined of recycling an ethyl benzene/ethyl cyclohexane stream to the dehydrogenation reactor. At an LHSV (liquid hourly space velocity) of 1 [hour$^{-1}$] and a molar ratio of feed/nitrogen of 1:3, a feed stream with 89.7 wt. % ethyl benzene and 10.3 wt. % ethyl cyclohexane was passed over the Pd/MgO dehydrogenation catalyst. At an inlet temperature of 250° C. the reaction product was composed of 91.9 wt. % ethyl benzene and 8.1 wt. % ethyl cyclohexane. At an inlet temperature of 300° C. the composition comprised 92.4 wt. % ethyl benzene and 7.6 wt. % ethyl cyclohexane. Ethyl cyclohexane was therefore found to be converted selectively to ethyl benzene, the conversion amounting to 21% at 250° C. and 26% at 300° C.

We claim:

1. A process for the preparation of an alkyl benzene comprising dehydrogenating a feed containing the corresponding alkenyl cyclohexene in the gas phase using a catalyst and in the presence of a diluent to obtain a reaction product comprising said alkylbenzene and an alkyl cyclohexane, wherein said feed contains alkenyl cyclohexene and alkyl cyclohexane in a molar ratio between 10:1 and 1:10 wherein at least a part of the alkyl cyclohexane in the reaction product is used as diluent.

2. A process according to claim 1, wherein at least a part of the hydrogen present in the reaction product is used as diluent.

3. A process according to claim 1 or 2, wherein the alkyl cyclohexane is obtained by a distillation from the reaction product.

4. A process according to claim 2, wherein the alkenyl cyclohexene/hydrogen molar ratio in the feed to the catalytic dehydrogenation has a value between 2:1 and 1:100.

5. A process according to claim 1, 2 or 4, wherein 4-vinyl cyclohexene is dehydrogenated to ethyl benzene.

6. A process according to claim 1, 2 or 4, wherein the reaction is carried out in an adiabatically operated reactor.

* * * * *